(12) United States Patent
Goodnow (10) Patent No.: US 9,278,142 B1
(45) Date of Patent: Mar. 8, 2016

(54) OPTIMUM CONDENSER WATER TEMPERATURE FOR WATER COOLED CHILLER

(71) Applicant: Amazon Technologies, Inc., Reno, NV (US)

(72) Inventor: Christopher A. Goodnow, Seattle, WA (US)

(73) Assignee: Amazon Technologies, Inc., Reno, NV (US)

( * ) Notice: Subject to any disclaimer, the term of this patent is extended or adjusted under 35 U.S.C. 154(b) by 811 days.

(21) Appl. No.: 13/622,321

(22) Filed: Sep. 18, 2012

(51) Int. Cl.
  *F25B 25/00* (2006.01)
  *A61K 48/00* (2006.01)
  *F24F 1/00* (2011.01)

(52) U.S. Cl.
  CPC .......... *A61K 48/00* (2013.01); *F24F 2001/0092* (2013.01)

(58) Field of Classification Search
  CPC . F24F 5/003; F24F 2001/0092; F25B 25/005; F25B 2339/041; F25B 2339/047
  USPC ........................................................ 62/259.4
  See application file for complete search history.

(56) References Cited

U.S. PATENT DOCUMENTS

| | | | | |
|---|---|---|---|---|
| 4,474,027 A | * | 10/1984 | Kaya et al. | 62/171 |
| 4,932,218 A | * | 6/1990 | Robbins | 62/171 |
| 8,223,495 B1 | * | 7/2012 | Carlson et al. | 361/701 |
| 2004/0011046 A1 | * | 1/2004 | Pierson | 60/772 |

* cited by examiner

*Primary Examiner* — Jonathan Bradford
(74) *Attorney, Agent, or Firm* — Kilpatrick Townsend & Stockton LLP (57) ABSTRACT

A computer-implemented method generates a set-point temperature for an evaporative cooler supplying cooled water to a chiller. Under the control of one or more computer systems configured with executable instructions, an achievable temperature for water supplied to the chiller by the evaporative cooler is generated based at least in part on an outside wet bulb temperature. A set-point temperature for the water supplied to the chiller by the evaporative cooler is then generated. The set-point temperature is the greater of the achievable temperature and a minimum temperature for water that can be used by the chiller without causing damage to the chiller.

24 Claims, 8 Drawing Sheets

OPTIMUM CONDENSER WATER TEMPERATURE FOR WATER COOLED CHILLER

BACKGROUND

The combination of a chiller and an evaporative cooler is often used to remove heat from a building, equipment, etc. In general, a chiller provides cooled water for cooling a building, equipment, etc., and an evaporative cooler provides water to the chiller for cooling heated return water. A first recirculation loop carries chilled water from the chiller to the building, equipment, etc., where the chilled water is used to extract the heat. After extracting the heat, the water is then recirculated back to the chiller. Heat is then removed from the recirculated water by the evaporative cooler. To this end, a second recirculation loop delivers cool water from the evaporative cooler to the chiller. The chiller transfers the heat from the recirculated water to the cool water from the evaporative cooler. The second recirculation loop then returns the now heated, evaporative cooler loop water to the evaporative cooler. The evaporative cooler removes the heat from the evaporative cooler loop water, thereby generating a continual supply of the cool water that is supplied to the chiller.

In addition to transferring heat by increasing the temperature of outside air, the evaporative cooler also increases the relative humidity of the air thereby transferring heat via the heat of vaporization. Therefore, the amount of heat that can be transferred by the evaporative cooler is dependent on both the temperature and the humidity of the outside air. Accordingly, for some outside conditions where the evaporative cooler cannot run as efficiently due to humidity, when the evaporative cooler is controlled to supply cool water to the chiller at a set temperature, the evaporative cooler will be driven at maximum capacity and the water that the evaporative cooler supplies to the chiller will exceed the set temperature.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. It will, however, also be apparent to one skilled in the art that the embodiments may be practiced without the specific details. Furthermore, well-known features may be omitted or simplified in order not to obscure the embodiment being described.

Techniques described and suggested herein include determining a set-point temperature for an evaporative cooler that supplies cool water to a chiller based at least in part on an outside wet bulb temperature such that the evaporative cooler is able to output cool water having the set-point temperature. In many embodiments, the set-point temperature is such that the evaporative cooler is able to output cool water having the set-point temperature while operating at less than 100 percent capacity. By selecting the set-point temperature based on the outside wet bulb temperature, the operational rate of the evaporative cooler can be controlled so as to reduce and even minimize total system power requirements, which include the power required to operate the chiller and the power required to operate the evaporative cooler.

Often, the chiller may be damaged if the cool water from the evaporative cooler has a temperature below a minimum temperature. For example, when the cool water has a temperature below the minimum temperature, oil migration in the refrigerant in the chiller may occur, which may result in damage to the chiller. The minimum temperature below which oil migration may occur can vary based on the operating parameters at which the chiller is being operated. For example, the minimum temperature may be a function of the operating load level of the chiller, the temperature of the chilled water produced by the chiller, and the evaporative delta temperature (the temperature difference between water entering and leaving the chiller from the evaporative cooler) at full load for the chiller. Accordingly, the set-point temperature for the evaporative cooler can be selected so as to not be less than the minimum temperature that can be tolerated by the chiller without resulting in damage to the chiller. This minimum temperature may be an actual minimum, or a minimum that is set for convenience, such as to take into account engineering safety.

The total power consumed by the combination of the chiller and the evaporative cooler can often be minimized by selecting an optimal operating level for the evaporative cooler. For a particular humidity and temperature of the outside air and a particular rate at which the chiller must remove heat from the water in the first recirculation loop, an increase in the operating level of the evaporative cooler will result in a decrease in the temperature of the cool water delivered to the chiller, thereby permitting a corresponding reduction in the power consumed to run the chiller. Likewise, a decrease in the operating level of the evaporative cooler decreases the power consumed to operate the evaporative cooler, but results in an increase in the temperature of the cooled water delivered to the chiller, thereby increasing the power consumed to run the chiller. Often, there can be an optimum rate at which to operate the evaporative cooler that minimizes the total amount of power required to operate both the chiller and the evaporative cooler. In many embodiments, the optimum rate at which to operate the evaporative cooler is less than 100 percent of the maximum operational rate for the evaporative cooler.

Figure 1:
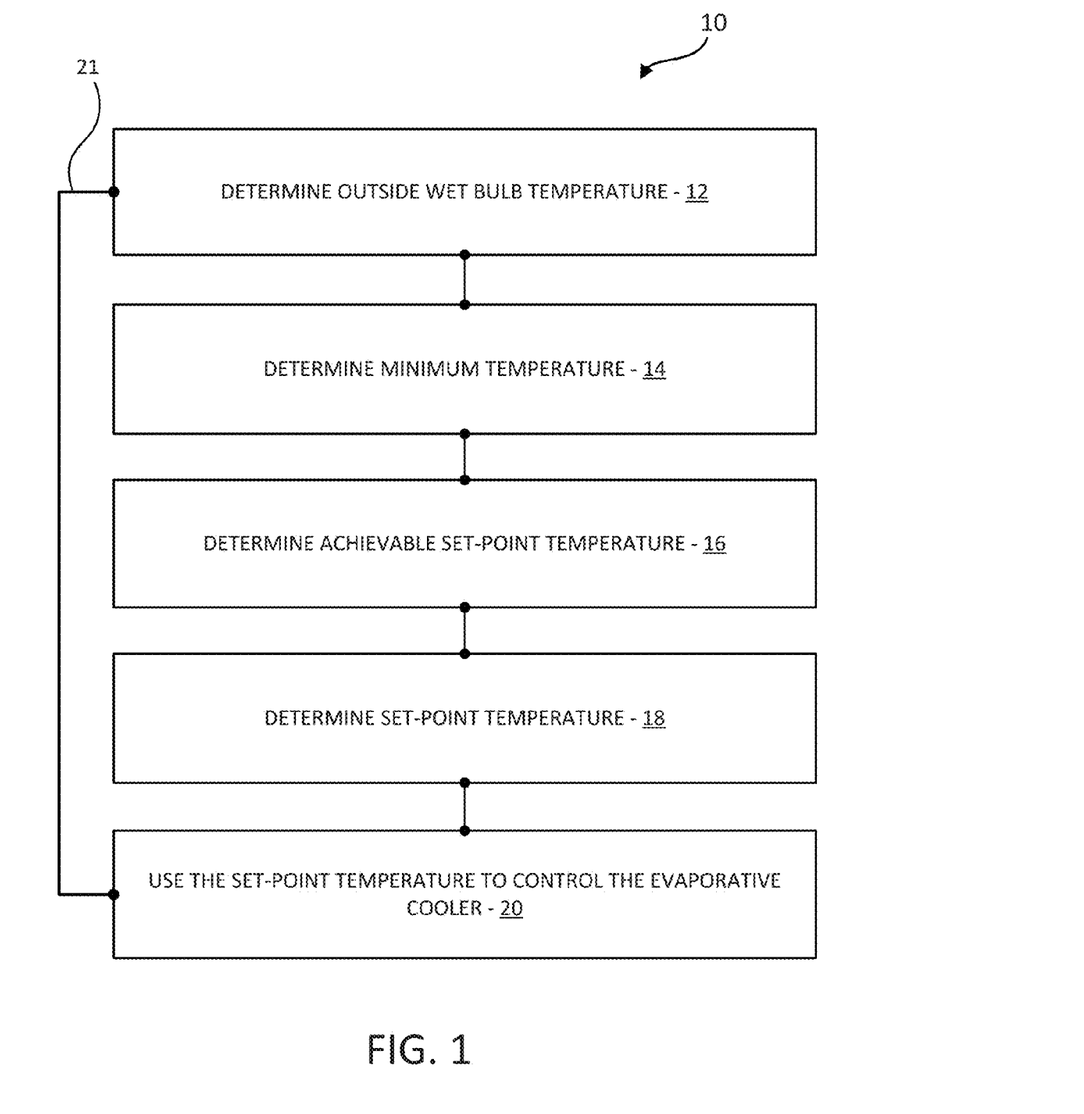
FIG. 1 is a simplified block diagram of a method, in accordance with many embodiments, for controlling an evaporative cooler that supplies cool water to a chiller.

Referring now to the drawings, in which like reference numerals represent like parts throughout the several views, FIG. 1 illustrates acts of a method 10 for controlling an evaporative cooler, in accordance with many embodiments. The method 10 can be practiced in conjunction with the systems described herein.

In act 12, an outside wet bulb temperature is determined for air that will be processed by the evaporative cooler. Any suitable method can be used to determine the outside wet bulb temperature. For example, the temperature and the humidity of the outside air can be measured and used to determine the wet bulb temperature using known methods. Additionally, the temperature and/or the humidity can be obtained from a suitable alternate source, such as via the internet. Likewise, the wet bulb temperature can be directly measured using known methods. And the wet bulb temperature can be obtained from a suitable alternate source, such as via the internet.

In many chillers, if the cooling water from the evaporative cooler is colder than the minimum temperature, migration of lubrication oil in the refrigerant in the chiller may result. Such migration of lubrication oil may result in damage to the chiller. In act 14, the minimum temperature of the cooling water from the evaporative cooler that can be processed by the chiller without damaging the chiller is determined using a suitable method. This number does not necessarily correspond exactly with a damage temperature for the chiller. For example, the minimum temperature can be conservatively set to be a single constant temperature suitable for all operating conditions of the chiller. A suitable minimum temperature can also be determined for each operating condition of the chiller.

In embodiments, for an exemplary chiller, a minimum temperature suitable for a particular operating condition can be based on the temperature of the chilled water output by the chiller, the evaporative delta temperature for the chiller at full load, and the operating load level of the chiller.

Embodiments herein utilize the following formula to calculate a minimum temperature:

$$Temp_{min} = 18.75 + Temp_{out} - (1.5 \times Evap_{delta_{temp}} \times (percent_{load_{chiller}}/100)) + (22.0 \times (percent_{load_{chiller}}/100)) + (\text{manufacturer offset}).$$

(Equation 1)

(Equation 1). Where:

$Temp_{min}$=the minimum temperature of the cool water received by the chiller from the evaporative cooler necessary to avoid oil migration and possible associated damage to the chiller $Temp_{out}$=temperature of the chilled water output by the chiller, in Fahrenheit $Evap_{delta\_temp}$=the evaporative delta temperature at full load for the chiller $percent\_load_{chiller}$=the operating load percentage for the chiller manufacturer offset=an offset that is provided to make sure that the evaporative cooler is operating within the safe temperatures defined by the chiller manufacturer As an example, where $Temp_{out}$=47 degrees Fahrenheit, $Evap_{delta\_temp}$=11.0 degrees Fahrenheit, and percent_ $load_{chiller}$=100.0%, the manufacturer offset is 9.5 degrees Fahrenheit, the minimum temperature $Temp_{min}$ is 71.25 degrees.

In act 16, an achievable set-point temperature for the evaporative cooler is determined. In many embodiments, the achievable set-point temperature is based at least in part on the outside wet bulb temperature. The achievable set-point temperature can also be based on an approach temperature for the evaporative cooler. The approach temperature for the evaporative cooler is the difference in temperature between the cool water produced by the evaporative cooler and the wet bulb temperature of the outside air. In many embodiments, the achievable set-point temperature is determined such that the evaporative cooler is operated at less than 100 percent. For example, in many embodiments the achievable set-point temperature is determined such that the evaporative cooler operates at a rate between 55 and 90 percent of its maximum operational rate. And in many embodiments, the achievable set-point temperature is determined such that the evaporative cooler operates at a rate between 65 and 80 percent of its maximum operational rate.

In many embodiments, the achievable set-point temperature for the evaporative cooler is a function of the minimum temperature as defined in equation (1), the outside wet bulb temperature, the approach temperature for the evaporative cooler, and an overall minimum temperature of water from the evaporative cooler that can be processed by the chiller without damage to the chiller. For example, the achievable set-point temperature for the evaporative cooler can be calculated using equation (2) below.

$$Temp_{acheivable\ set\ point}=(\text{offset ratio}\times Temp_{min}^{min})+Temp_{approach}$$

(Equation 2)

Where:

$Temp_{acheivable\ set\ point}$=achievable set-point temperature offset ratio=$((Temp_{wet-bulb}+Temp_{approach})/Temp_{min})$ $Temp_{wet-bulb}$=the outside wet bulb temperature $Temp_{approach}$=the evaporative cooler approach temperature $Temp_{min}$=from equation (1)

$Temp_{min}^{min}$=the overall minimum temperature of water from the evaporative cooler that can be processed by the chiller without damage to the chiller As an example, where the $Temp_{wet-bulb}$=60 degrees Fahrenheit, the $Temp_{approach}$ is 8.0 degrees Fahrenheit, and the $Temp_{min}$=71.25, as calculated above, then the offset ratio= $((Temp_{wet-bulb}+Temp_{approach})/Temp_{min})$=0.9544.

Further to the example, if $Temp_{min}^{min}$=65 degrees Fahrenheit, the $Temp_{acheivable\ set\ point}$=(offset ratio×$Temp_{min}^{min}$)+ $Temp_{approach}$=70.04 degrees Fahrenheit.

Notably, the achievable temperature set-point resulting from the sample calculation above is 2.04 degrees Fahrenheit higher than 68.0 degrees Fahrenheit, which is the approach temperature for the evaporative cooler added to the outside wet bulb temperature. Because the achievable set point temperature is higher than the approach temperature for the evaporative cooler added to the outside wet bulb temperature, the evaporative cooler will work at less than 100 percent capacity to output water having the achievable set point temperature.

In act 18, the set-point temperature to be used to control the evaporative cooler is determined. In many embodiments, the set-point temperature is selected to be the greater of the minimum temperature of the cool water received by the chiller from the evaporative cooler necessary to avoid oil migration and possible associated damage to the chiller as calculated in equation (1) and the achievable set-point temperature as calculated in equation (2) above.

In act 20, the set-point temperature is used to control the evaporative cooler. Accordingly, the evaporative cooler is controlled by a set point temperature that is achievable, as opposed to being run at 100% capacity whenever the outside conditions are not conducive for the evaporative cooler to try to output water at an unachievably low temperature given the outside ambient temperature and humidity. As indicated by process flow line 21 in FIG. 1, the acts 12, 14, 16, 18, 20 of the method 10 can be repeatedly accomplished to control the evaporative cooler.

Figure 1A:
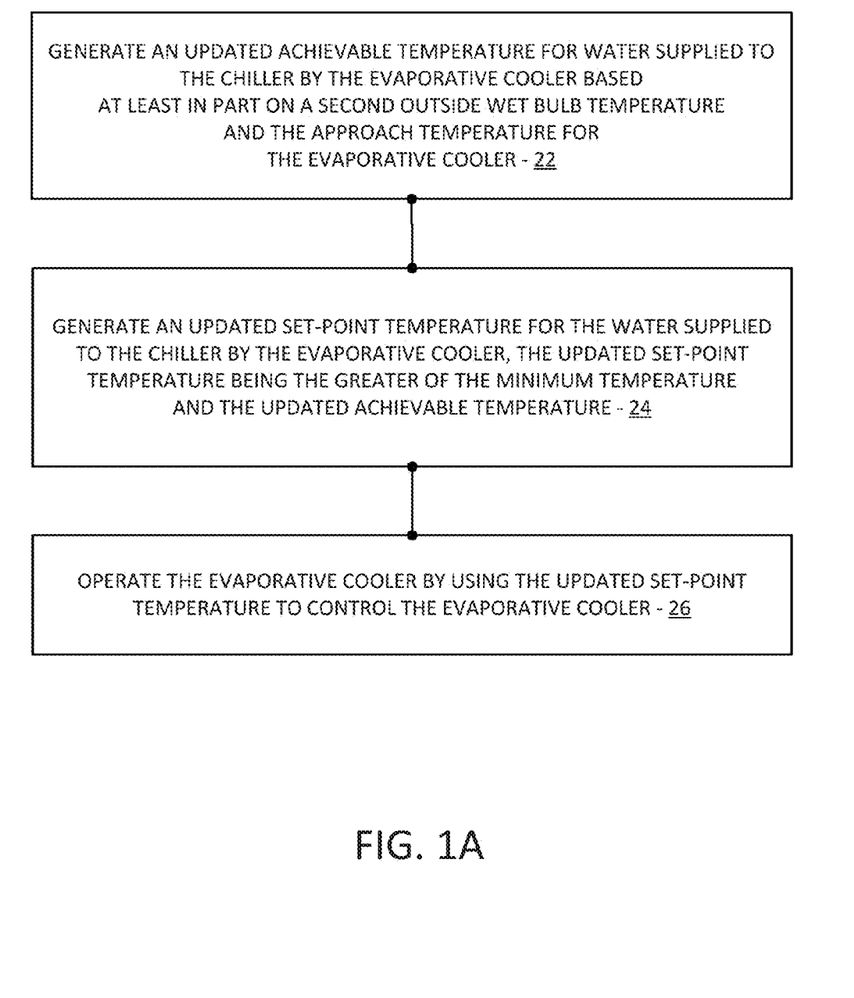
FIG. 1A is a simplified block diagram of optional acts that can be accomplished in the method of FIG. 1 for controlling the evaporative cooler.

FIG. 1A is a simplified block diagram of optional acts that can be accomplished in the method 10 under the control of one or more computer systems configured with executable instructions. In act 22, an updated achievable temperature for water supplied to the chiller by the evaporative cooler is generated based at least in part on a second outside wet bulb temperature and the approach temperature for the evaporative cooler. In act 24, an updated set-point temperature for the water supplied to the chiller by the evaporative cooler is generated, the updated set-point temperature being the greater of the minimum temperature and the updated achievable temperature. In act 26, the evaporative cooler is operated by using the updated set-point temperature to control the evaporative cooler.

Figure 2:
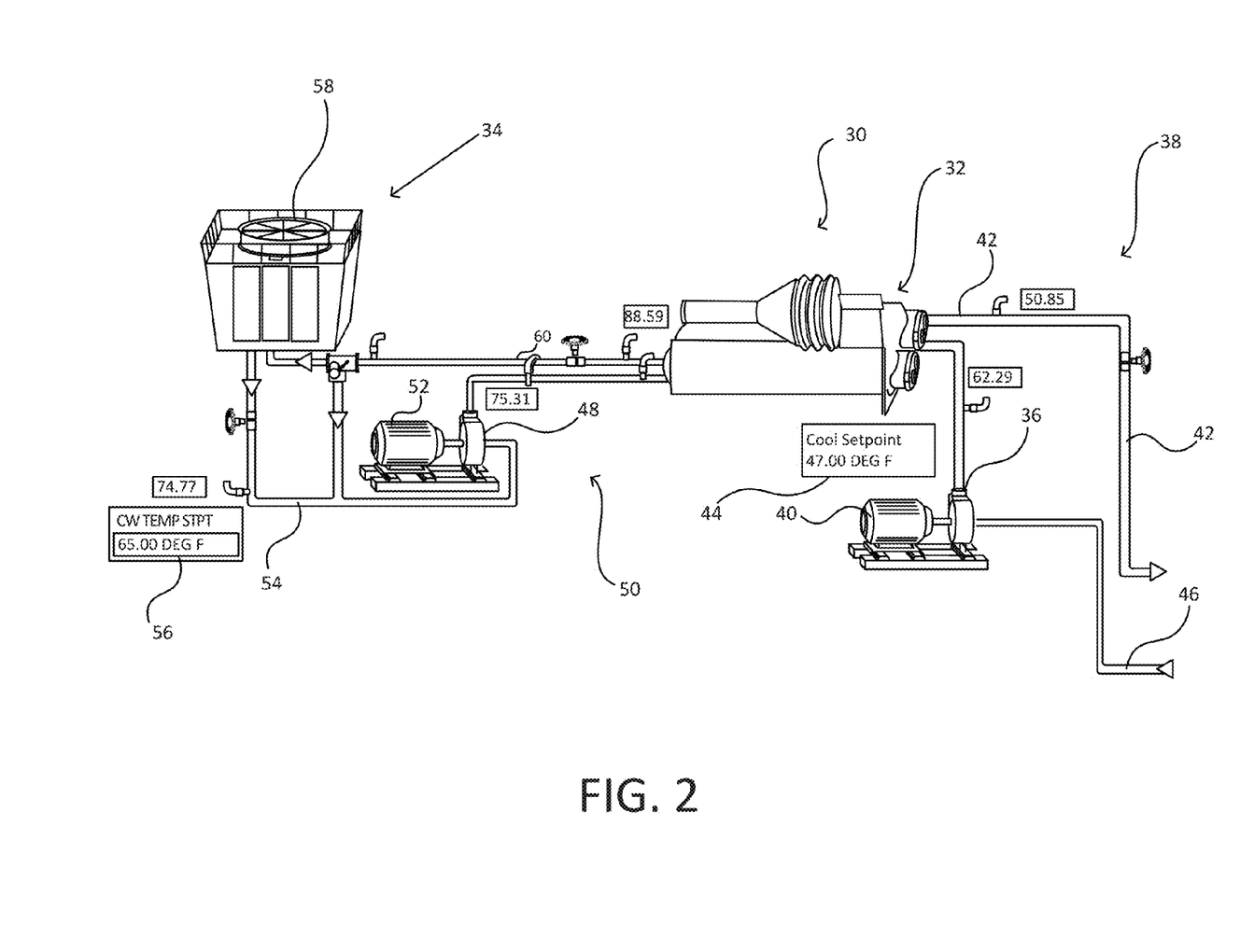
FIG. 2 is a schematic diagram illustrating components of a cooling system that includes a chiller and an evaporative cooler, in accordance with many embodiments.

FIG. 2 is a schematic diagram illustrating components of a cooling system 30 that includes a chiller 32 and an evaporative cooler 34, in accordance with many embodiments. A first recirculation pump 36 circulates water in a first recirculation loop 38 between the chiller 32 and an item from which heat is being extracted. The first recirculation pump 36 is driven by a motor 40. In many embodiments, the motor 40 is a variable speed motor, thereby allowing selective control of the flow rate of the water in the first recirculation loop 38. The chiller 32 outputs chilled water into an output line 42, which carries the chilled water to the item being cooled. The chiller 32 is controlled so as to output chilled water at a chilled water set-point temperature 44, for example, by varying the operational rate of the chiller 32. After absorbing heat from the item being cooled, the water is returned to the chiller 32 via a return line 46.

A second recirculation pump 48 circulates water in a second recirculation loop 50 between the evaporative cooler 34 and the chiller 32. The second recirculation pump 48 is driven by a motor 52. In many embodiments, the motor 52 is a variable speed motor, thereby allowing selective control of the flow rate of the water in the second recirculation loop 50. The evaporative cooler 34 outputs cool water into an output line 54, which carries the cool water to the chiller 32. The evaporative cooler 34 is controlled so as to attempt to output cool water at a cool water set-point temperature 56. For example, the evaporative cooler 34 includes a fan 58, the operational rate of which is varied so as to attempt to output cool water at the cool water set-point temperature 56. After absorbing heat from the chiller 32, the water is returned to the evaporative cooler 34 via a return line 60.

In operation, the chiller 32 and the motor 40 are controlled to supply chilled water to the item being cooled at a temperature and rate suitable to achieve the desired rate of cooling of the item being cooled. For example, the chilled water set-point temperature 44 can be selected consistent with the desired rate of cooling. Additionally, when the motor 40 is a variable speed motor, the rotational speed of the motor 40 can be selected to produce a desired recirculation rate for the water in the first recirculation loop 38.

The evaporative cooler 34 is controlled to attempt to supply cool water to the chiller at the cool water set-point temperature 56. The ability of the evaporative cooler 34 to actually output cool water to the chiller 32 at the cool water set-point temperature 56, however, depends upon the outside ambient conditions, and particularly on the outside wet bulb temperature. When the outside wet bulb temperature is too high, the evaporative cooler 34 may output cool water to the chiller 32 at a temperature exceeding the cool water set-point temperature 56 despite operating at full capacity (100 percent fan speed). Accordingly, the cool water set-point temperature 56 is selected based at least in part on the outside wet bulb temperature so that the evaporative cooler 34 is capable of outputting cool water at the cool water set-point temperature 56 for the particular outside ambient conditions.

Figure 3:
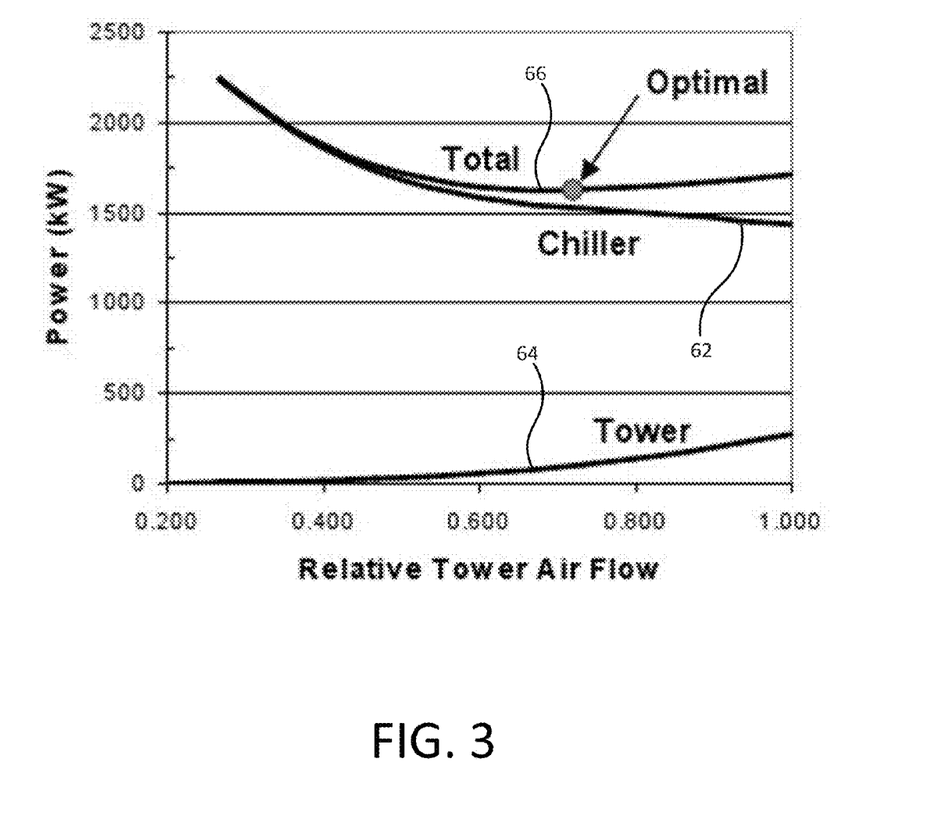
FIG. 3 illustrates power usage rates for a cooling system that includes a chiller and an evaporative cooler for different operating rates for the evaporative cooler, in accordance with many embodiments.

FIG. 3 is a graph showing the power 62 to operate the chiller 32, the power 64 to operate the evaporative cooler 34, the combined power 66 to operate both the chiller 32 and the evaporative cooler 34 for an example combination of load on the chiller 32 and outside ambient condition for a range of operational rates of the evaporative cooler 34. As shown in the graph, for this particular example load on the chiller 32 and outside ambient condition, running the evaporative cooler 34 at maximum rate (relative tower airflow equal to 1.000) does not minimize the combined power 66. Instead, by reducing the operational rate of the evaporative cooler 34 to be less than the maximum possible rate, the combined power 66 can be reduced with the lowest combined power 66 occurring at approximately seventy percent operational rate of the evaporative cooler 34. Notably, the combined power 66 curve is relatively flat near the optimal value, thereby allowing a fairly broad range of operational rates for the evaporative cooler 34 to be used while substantially minimizing the combined power 66.

Figure 4:
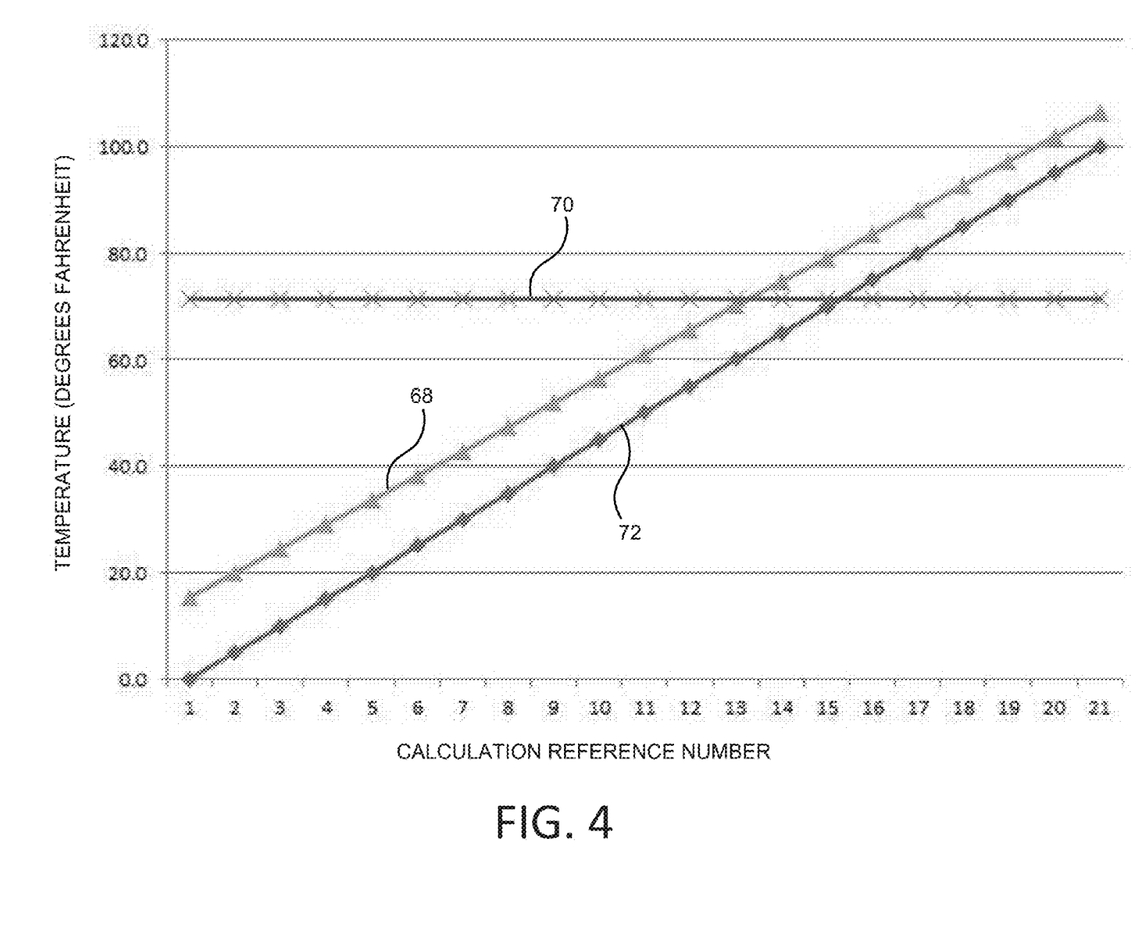
FIG. 4 illustrates achievable temperature set-points for an evaporative cooler and a minimum acceptable temperature for cool water supplied to a chiller operating at 100 percent load for a range of outside wet bulb temperatures, in accordance with many embodiments.
Figure 5:
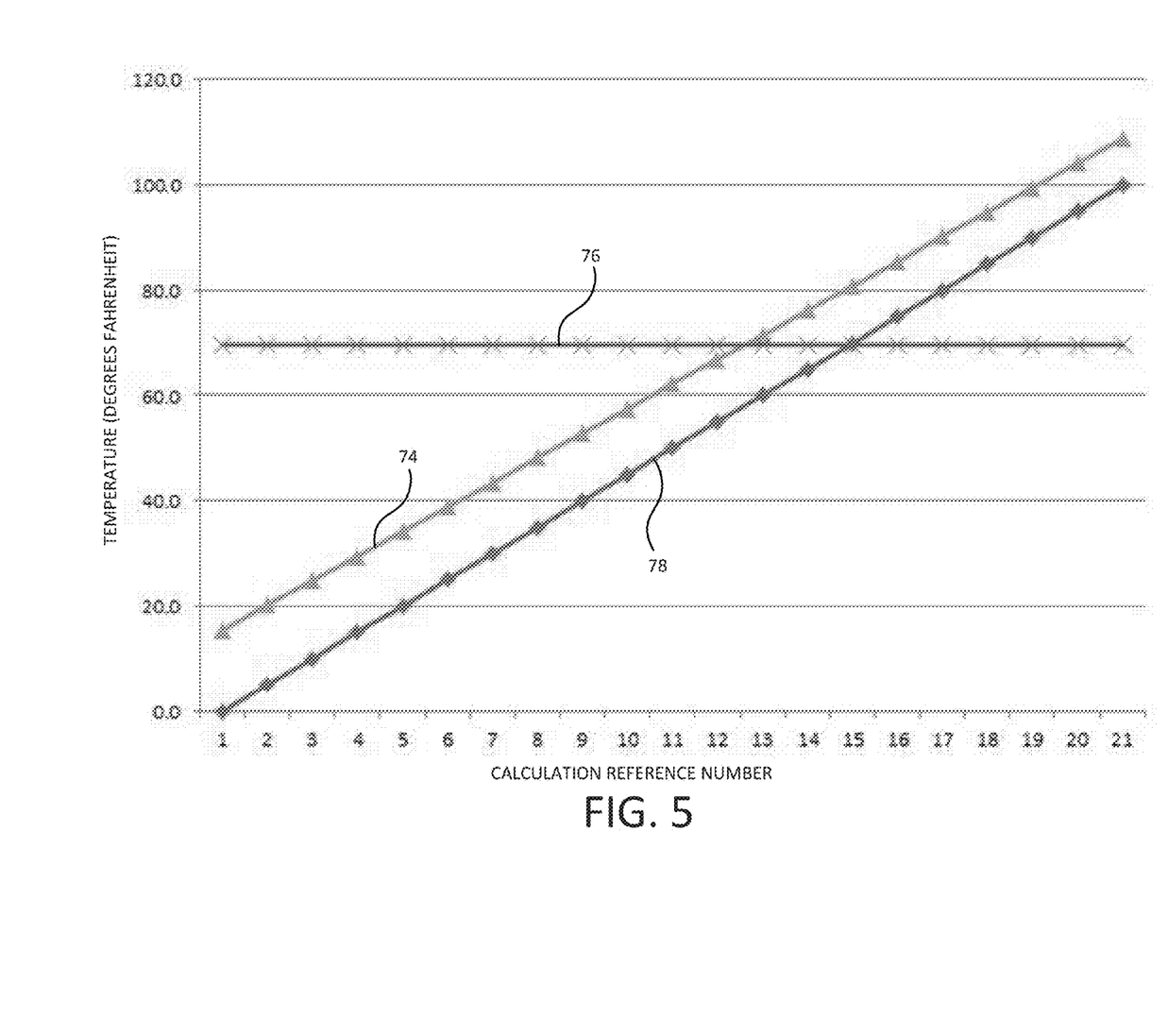
FIG. 5 illustrates achievable temperature set-points for an evaporative cooler and a minimum acceptable temperature for cool water supplied to a chiller operating at 70 percent load for a range of outside wet bulb temperatures, in accordance with many embodiments.
Figure 6:
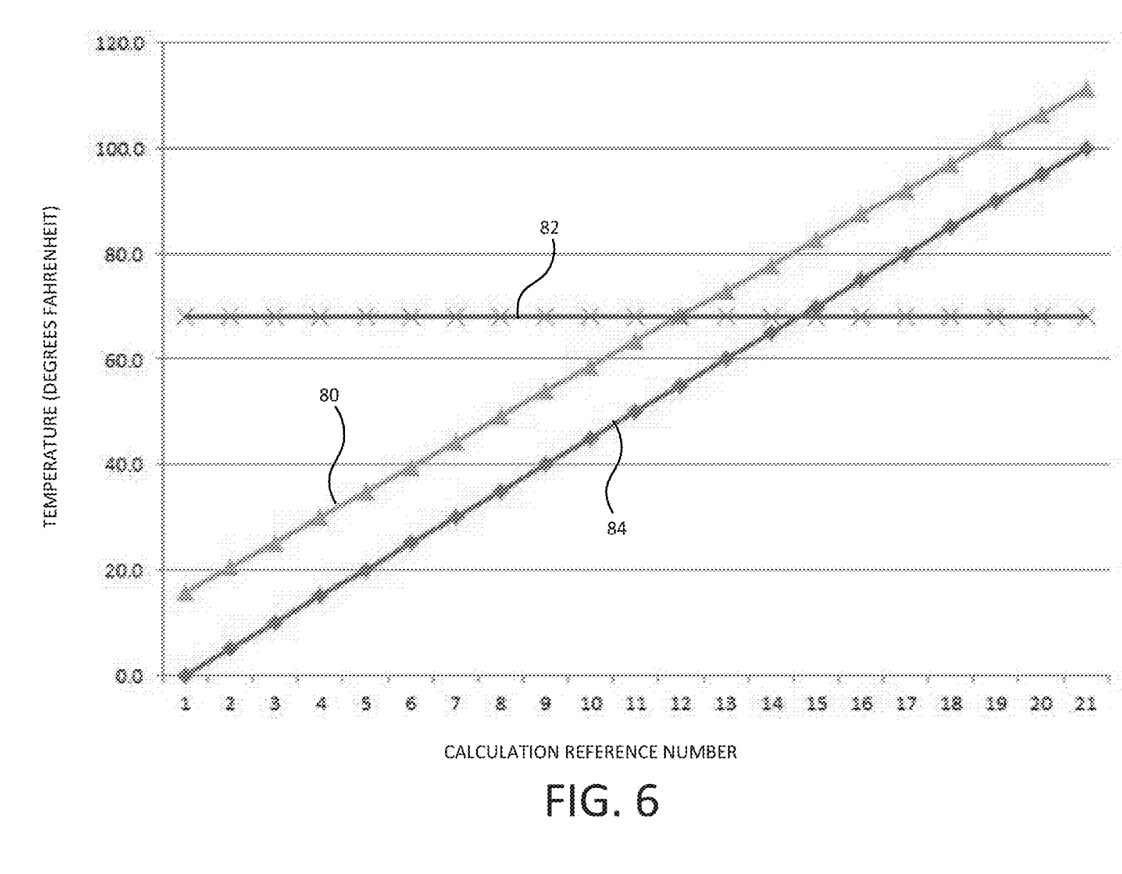
FIG. 6 illustrates achievable temperature set-points for an evaporative cooler and a minimum acceptable temperature for cool water supplied to a chiller operating at 40 percent load for a range of outside wet bulb temperatures, in accordance with many embodiments.

FIGS. 4 through 6 illustrate achievable set-point temperatures (calculated using Equation 2) for the evaporative cooler 34 and minimum acceptable temperatures (calculated using Equation 1) for cool water supplied to the chiller 32 operating at three different load levels for a range of outside wet bulb temperatures with a chilled water temperature of 47 degrees Fahrenheit and an evaporative delta temperature at full load for the chiller 32 of 11 degrees Fahrenheit. FIG. 4 illustrates achievable set-point temperatures 68 for the evaporative cooler 34 and a minimum acceptable temperature 70 (71.25 degrees Fahrenheit) for cool water supplied to the chiller 32 operating at one-hundred percent chiller load for a range of outside wet bulb temperatures 72. FIG. 5 illustrates achievable set-point temperatures 74 for the evaporative cooler 34 and a minimum acceptable temperature 76 (69.6 degrees Fahrenheit) for cool water supplied to the chiller 32 operating at seventy percent chiller load for a range of outside wet bulb temperatures 78. FIG. 6 illustrates achievable set-point temperatures 80 for the evaporative cooler 34 and a minimum acceptable temperature 82 (67.95 degrees Fahrenheit) for cool water supplied to the chiller 32 operating at forty percent chiller load for a range of outside wet bulb temperatures 84. As shown, when the outside wet bulb temperature is below a certain value, the evaporative cooler 34 is capable of outputting cool water to the chiller 32 at below the minimum acceptable temperature. Therefore, in many embodiments, when the achievable set-point temperature is below the minimum acceptable temperature, the minimum acceptable temperature is used as the cool water set-point temperature to control the evaporative cooler.

Some or all of the method 10 (or any other methods described herein, or variations and/or combinations thereof) may be performed under the control of one or more computer systems, which include computer controllers for the motors, chillers, and evaporative cooler described herein, configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Figure 7:
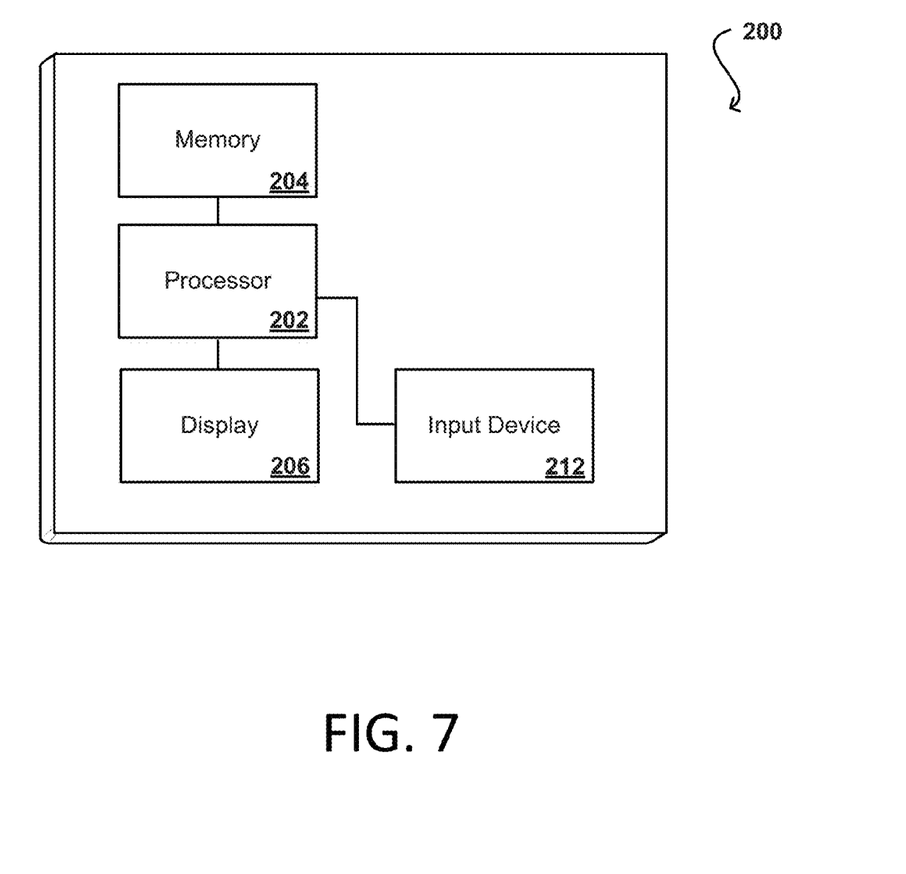
FIG. 7 illustrates an environment in which various embodiments can be implemented.

Operations herein can be performed via a computing system, including one or more motor and device controllers for operating the components of the system described herein. FIG. 7 illustrates a set of basic components of a computing device 200 that may be used for such functions. Although a single computing device is shown, the operations of the computing device 200 may be distributed over multiple computing devices, and one or more of the computing devices may be located remotely. In this example, the device includes a processor 202 for executing instructions that can be stored in a memory device or element 204. As would be apparent to one of ordinary skill in the art, the device can include many types of memory, data storage, or computer-readable media, such as a first data storage for program instructions for execution by the processor 202, a separate storage for images or data, a removable memory for sharing information with other devices, etc. The device typically can include some type of display element 206, such as a touch screen or liquid crystal display (LCD), although devices such as motor controllers might operate without a display. The devices herein can also include an input device 212 able to receive conventional input and commands from a user, such as a technician or an operator. This conventional input can include, for example, a push button, touch pad, touch screen, wheel, joystick, keyboard, mouse, keypad, or any other such device or element whereby a user can input a command to the device. In some embodiments, however, such a device might not include any local input devices at all, and might be controlled remotely through another computer system, as an example.

As previously described, various embodiments can be further implemented in a wide variety of operating environments, which in some cases can include one or more user computers or computing devices which can be used to operate any of a number of applications or software instructions. User or client devices used to program and maintain the instructions herein can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, and other devices capable of communicating via a network.

Embodiments that utilize a network that would be familiar to those skilled in the art for can support communications using any of a variety of commercially-available protocols, such as TCP/IP, OSI, FTP, UPnP, NFS, CIFS and AppleTalk. The network can be, for example, a local area network, a wide-area network, a virtual private network, the Internet, an intranet, an extranet, a public switched telephone network, an infrared network, a wireless network and any combination thereof In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device.

Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A computer-implemented method for controlling an evaporative cooler supplying cooled water to a chiller, the method comprising:
   under the control of one or more computer systems configured with executable instructions,
      generating an achievable temperature for water supplied to the chiller by the evaporative cooler based at least in part on an outside wet bulb temperature and an approach temperature for the evaporative cooler;
      generating a set-point temperature for the water supplied to the chiller by the evaporative cooler, the set-point temperature being the greater of the achievable temperature and a minimum temperature; and
      operating the evaporative cooler by using the set-point temperature to control the evaporative cooler.

2. The computer-implemented method of claim 1, wherein the minimum temperature comprises a low temperature limit for avoidance of oil migration in a refrigerant in the chiller.

3. The computer-implemented method of claim 1, wherein the achievable temperature corresponds to an operational level of the evaporative cooler in a range of 55 percent to 90 percent of the maximum operational level of the evaporative cooler.

4. The computer-implemented method of claim 3, wherein the achievable temperature corresponds to an operational level of the evaporative cooler in a range of 65 percent to 80 percent of the maximum operational level of the evaporative cooler.

5. The computer-implemented method of claim 1, further comprising:
   under the control of one or more computer systems configured with executable instructions,
      generating an updated achievable temperature for water supplied to the chiller by the evaporative cooler based at least in part on a second outside wet bulb temperature and the approach temperature for the evaporative cooler;
      generating an updated set-point temperature for the water supplied to the chiller by the evaporative cooler, the updated set-point temperature being the greater of the minimum temperature and the updated achievable temperature; and
      operating the evaporative cooler by using the updated set-point temperature to control the evaporative cooler.

6. The computer-implemented method of claim 1, wherein the achievable temperature is equal to the outside wet bulb temperature plus a temperature offset that varies as a function of the minimum temperature, the outside wet bulb temperature, and the approach temperature for the evaporative cooler.

7. A computer-implemented method for generating a set-point temperature for an evaporative cooler supplying cooled water to a chiller, the method comprising:
   under the control of one or more computer systems configured with executable instructions,
      generating an achievable temperature for water supplied to the chiller by the evaporative cooler based at least in part on an outside wet bulb temperature; and
      generating a set-point temperature for the water supplied to the chiller by the evaporative cooler, the set-point temperature being the greater of the achievable temperature and a minimum temperature.

8. The computer-implemented method of claim 7, wherein the minimum temperature comprises a low temperature limit for avoidance of oil migration in a refrigerant in the chiller.

9. The computer-implemented method of claim 7, wherein the achievable temperature corresponds to an operational level of the evaporative cooler in a range of 55 percent to 90 percent of the maximum operational level of the evaporative cooler.

10. The computer-implemented method of claim 7, wherein the minimum temperature is calculated via:

$$Temp_{min} = 18.75 + Temp_{out} - (1.5 \times Evap_{delta_{temp}} \times (percent_{load_{chiller}} / 100)) + (22.0 \times (percent_{load_{chiller}} / 100)) + (\text{manufacturer offset})$$

Where:
$Temp_{min}$=the minimum temperature of the cool water received by the chiller from the evaporative cooler necessary to avoid oil migration and possible associated damage to the chiller;
$Temp_{out}$=temperature of the chilled water output by the chiller, in Fahrenheit;
$Evap_{delta\_temp}$=the evaporative delta temperature at full load for the chiller;
$percent\_load_{chiller}$=the operating load percentage for the chiller; and
manufacturer offset=an offset that is provided to make sure that the evaporative cooler is operating within the safe temperatures defined by the chiller manufacturer.

11. The computer-implemented method of claim 7, further comprising:
under the control of one or more computer systems configured with executable instructions,
generating an updated achievable temperature for water supplied to the chiller by the evaporative cooler based at least in part on an updated outside wet bulb temperature; and
generating an updated set-point temperature for the water supplied to the chiller by the evaporative cooler, the updated set-point temperature being the greater of the minimum temperature and the updated achievable temperature.

12. The computer-implemented method of claim 7, wherein the achievable temperature is equal to the outside wet bulb temperature plus a temperature offset that varies as a function of the minimum temperature, the outside wet bulb temperature, and an approach temperature for the evaporative cooler.

13. A system for supplying cooled water to a chiller, the system comprising:
an evaporative cooler for coupling with a chiller to supply cooled water to the chiller and to receive return water from the chiller;
an outside wet bulb temperature source that supplies an outside wet bulb temperature; and
one or more computer systems configured with executable instructions to,
generate an achievable temperature for water supplied to the chiller by the evaporative cooler based at least in part on an outside wet bulb temperature; and
generate a set-point temperature for the water supplied to the chiller by the evaporative cooler, the set-point temperature being the greater of the achievable temperature and a minimum temperature.

14. The system of claim 13, wherein the one or more computer systems are configured with executable instructions to operate the evaporative cooler by using the set-point temperature to control the evaporative cooler.

15. The system of claim 13, wherein the achievable temperature corresponds to an operational level of the evaporative cooler in a range of 55 percent to 90 percent of the maximum operational level of the evaporative cooler.

16. The system of claim 15, wherein the achievable temperature corresponds to an operational level of the evaporative cooler in a range of 65 percent to 80 percent of the maximum operational level of the evaporative cooler.

17. The system of claim 13, wherein the one or more computer systems are configured with executable instructions to:
generate an updated achievable temperature for water supplied to the chiller by the evaporative cooler based at least in part on an outside wet bulb temperature; and
generate an updated set-point temperature for the water supplied to the chiller by the evaporative cooler, the updated set-point temperature being the greater of the minimum temperature and the updated achievable temperature.

18. The system of claim 13, wherein the achievable temperature is equal to the outside wet bulb temperature plus a temperature offset that varies as a function of the minimum temperature for water supplied to the chiller, the outside wet bulb temperature, and the approach temperature for the evaporative cooler.

19. A non-transitory tangible computer readable medium storing instructions executable by one or more computer systems to generate a set-point temperature for an evaporative cooler supplying cooled water to a chiller, the instructions operable to cause the one or more computer systems to:
generate an achievable temperature for water supplied to the chiller by the evaporative cooler based at least in part on an outside wet bulb temperature; and
generate a set-point temperature for the water supplied to the chiller by the evaporative cooler, the set-point temperature being the greater of the achievable temperature and a minimum temperature.

20. The computer readable medium of claim 19, wherein the instructions are further operable to cause the one or more computer systems to operate the evaporative cooler by using the set-point temperature to control the evaporative cooler.

21. The computer readable medium method of claim 19, wherein the achievable temperature corresponds to an operational level of the evaporative cooler in a range of 55 percent to 90 percent of the maximum operational level of the evaporative cooler.

22. The computer readable medium method of claim 21, wherein the minimum temperature is calculated via:

$$Temp_{min} = 18.75 + Temp_{out} - (1.5 \times Evap_{delta_{temp}} \times (percent_{load_{chiller}} / 100)) + (22.0 \times (percent_{load_{chiller}} / 100)) + (\text{manufacturer offset})$$

Where:
$Temp_{min}$=the minimum temperature of the cool water received by the chiller from the evaporative cooler necessary to avoid oil migration and possible associated damage to the chiller;
$Temp_{out}$=temperature of the chilled water output by the chiller, in Fahrenheit;
$Evap_{delta\_temp}$=the evaporative delta temperature at full load for the chiller;
$percent\_load_{chiller}$=the operating load percentage for the chiller; and manufacturer offset=an offset that is provided to make sure that the evaporative cooler is operating within the safe temperatures defined by the chiller manufacturer.

23. The computer readable medium of claim 19, wherein the instructions are further operable to cause the one or more computer systems to:

generate an updated achievable temperature for water supplied to the chiller by the evaporative cooler based at least in part on an outside wet bulb temperature; and generate an updated set-point temperature for the water supplied to the chiller by the evaporative cooler, the set-point temperature being the greater of the updated achievable temperature and the minimum temperature.

24. The computer readable medium of claim 19, wherein the achievable temperature is equal to the outside wet bulb temperature plus a temperature offset that varies as a function of the minimum temperature for water supplied to the chiller, the outside wet bulb temperature, and an approach temperature for the evaporative cooler.

* * * * *